(12) United States Patent
Cheung et al.

(10) Patent No.: US 8,323,644 B2
(45) Date of Patent: *Dec. 4, 2012

(54) THERAPY-ENHANCING GLUCAN

(75) Inventors: Nai-Kong V. Cheung, Purchase, NY (US); Rolf Einar Engstad, Tromsø (NO)

(73) Assignees: Sloan-Kettering Institute for Cancer Research, New York, NY (US); Biotec Pharmacon ASA (NO)

( * ) Notice: Subject to any disclaimer, the term of this patent is extended or adjusted under 35 U.S.C. 154(b) by 0 days.

This patent is subject to a terminal disclaimer.

(21) Appl. No.: 12/161,285

(22) PCT Filed: Jan. 17, 2007

(86) PCT No.: PCT/US2007/001427
§ 371 (c)(1), (2), (4) Date: Jul. 17, 2008

(87) PCT Pub. No.: WO2007/084661
PCT Pub. Date: Jul. 26, 2007

(65) Prior Publication Data
US 2009/0004201 A1  Jan. 1, 2009

(51) Int. Cl.
*A61K 39/395* (2006.01)
*A61K 31/716* (2006.01)
*C07K 16/28* (2006.01)
*C07K 16/30* (2006.01)

(52) U.S. Cl. ............... 424/130.1; 424/137.1; 424/138.1; 424/141.1; 424/143.1; 424/144.1; 424/153.1; 424/155.1; 424/156.1; 514/54; 530/387.1; 530/387.5; 530/387.7; 530/387.9; 530/388.1; 530/388.22; 530/388.7; 530/388.75; 530/388.8; 536/123.12

(58) Field of Classification Search .................. None
See application file for complete search history.

(56) References Cited

U.S. PATENT DOCUMENTS

| | | |
|---|---|---|
| 3,975,553 A | 8/1976 | Griffon |
| 3,987,166 A | 10/1976 | Komatsu et al. |
| 4,251,519 A | 2/1981 | Robbins et al. |
| 4,343,784 A | 8/1982 | Massot et al. |
| 4,454,289 A | 6/1984 | Nakajima et al. |
| 4,705,780 A | 11/1987 | Massot et al. |
| 4,761,402 A | 8/1988 | Williams et al. |
| 4,810,646 A | 3/1989 | Jamas et al. |
| 4,818,752 A | 4/1989 | Williams et al. |
| 4,833,131 A | 5/1989 | Williams et al. |
| 4,900,722 A | 2/1990 | Williams et al. |
| 4,926,094 A | 5/1990 | Bondeson et al. |
| 4,992,540 A | 2/1991 | Jamas et al. |
| 5,032,401 A | 7/1991 | Jamas et al. |
| 5,037,972 A | 8/1991 | Jamas et al. |
| 5,130,127 A | 7/1992 | Herlyn |
| 5,189,028 A | 2/1993 | Nikl et al. |
| 5,223,491 A | 6/1993 | Donzis |
| 5,250,436 A | 10/1993 | Jamas et al. |
| 5,504,079 A | 4/1996 | Jamas et al. |
| 5,519,009 A | 5/1996 | Donzis |
| 5,532,223 A | 7/1996 | Jamas et al. |
| 5,576,015 A | 11/1996 | Donzis |
| 5,607,677 A | 3/1997 | Jamas et al. |
| 5,610,280 A | 3/1997 | Brandt et al. |
| 5,614,242 A | 3/1997 | Fox |
| 5,622,939 A | 4/1997 | Jamas et al. |
| 5,622,940 A | 4/1997 | Ostroff |
| 5,696,079 A | 12/1997 | Lane et al. |
| 5,702,719 A | 12/1997 | Donzis |
| 5,726,023 A | 3/1998 | Cheever et al. |
| 5,736,137 A | 4/1998 | Anderson et al. |
| 5,741,495 A | 4/1998 | Jamas et al. |
| 5,783,569 A | 7/1998 | Jamas et al. |
| 5,801,236 A | 9/1998 | Kamb |
| 5,804,199 A | 9/1998 | Aasjord et al. |
| 5,811,542 A | 9/1998 | Jamas et al. |
| 5,817,643 A | 10/1998 | Jamas et al. |
| 5,849,720 A | 12/1998 | Jamas et al. |
| 5,935,821 A | 8/1999 | Chatterjee et al. |
| 5,980,918 A | 11/1999 | Klein |
| 6,020,324 A | 2/2000 | Jamas et al. |
| 6,117,850 A | 9/2000 | Patchen et al. |
| 6,143,731 A | 11/2000 | Jamas et al. |
| 6,143,883 A | 11/2000 | Lehmann et al. |
| 6,180,614 B1 | 1/2001 | Davis |
| 6,217,866 B1 | 4/2001 | Schlessinger et al. |
| 6,369,216 B1 | 4/2002 | Patchen et al. |

(Continued)

FOREIGN PATENT DOCUMENTS

DE  30 19 614 A1  12/1981

(Continued)

OTHER PUBLICATIONS

Lehne et al (Clinical and Experimental Immunology, 2005, vol. 143, pp. 65-69).*

(Continued)

*Primary Examiner* — Karen Canella
(74) *Attorney, Agent, or Firm* — Law Offices of Albert Wai-Kit Chan, PLLC (57) ABSTRACT

A therapeutic composition for treatment of cancer in a mammal is disclosed. The composition comprises an effective amount of a yeast beta-glucan composition which is suitable for oral administration and for absorption through the gastrointestinal tract of the mammal. The above therapeutic composition may further comprise antitumor antibodies or cancer vaccine composition, wherein the antitumor activities of the antitumor antibodies or the cancer vaccine composition are enhanced by the yeast glucan.

14 Claims, 4 Drawing Sheets

U.S. PATENT DOCUMENTS

| | | | |
|---|---|---|---|
| 6,573,245 | B1 | 6/2003 | Marciani |
| 6,664,370 | B2 | 12/2003 | Cheever |
| 7,011,845 | B2 | 3/2006 | Kozbor et al. |
| 7,030,101 | B2 | 4/2006 | Pavliak et al. |
| 7,070,778 | B2 | 7/2006 | Yvin et al. |
| 2002/0044919 | A1 | 4/2002 | Yu |
| 2002/0119928 | A1 | 8/2002 | McAnalley |
| 2002/0160014 | A1 | 10/2002 | Rodriguez et al. |
| 2003/0180254 | A1 | 9/2003 | Lane et al. |
| 2004/0109857 | A1 | 6/2004 | Chu et al. |
| 2004/0116379 | A1 | 6/2004 | Cheung |
| 2004/0142000 | A1 | 7/2004 | Suga et al. |
| 2004/0248772 | A1 | 12/2004 | Yagita |
| 2004/0266726 | A1 | 12/2004 | Yagita |
| 2005/0118187 | A1 | 6/2005 | Yu |
| 2005/0208079 | A1 | 9/2005 | Cassone et al. |
| 2006/0009419 | A1 | 1/2006 | Ross et al. |
| 2006/0020128 | A1 | 1/2006 | Cheung |
| 2006/0160766 | A1 | 7/2006 | Cheung |
| 2006/0165700 | A1 | 7/2006 | Ostroff et al. |
| 2006/0188506 | A1 | 8/2006 | Cheung |
| 2006/0263355 | A1 | 11/2006 | Quan et al. |
| 2007/0020232 | A1 | 1/2007 | Rossignol et al. |
| 2007/0059310 | A1 | 3/2007 | Karel |
| 2007/0134259 | A1 | 6/2007 | Bundle et al. |

FOREIGN PATENT DOCUMENTS

| | | |
|---|---|---|
| EP | 0194851 A2 | 9/1986 |
| EP | 0463540 A1 | 2/1992 |
| EP | 0 759 089 B1 | 4/1995 |
| JP | 62252730 A2 | 11/1987 |
| JP | 63-500805 | 3/1988 |
| JP | 63307825 A2 | 12/1988 |
| WO | WO 91/03248 | 3/1991 |
| WO | WO 95/30022 | 11/1995 |
| WO | WO 98/39013 | 9/1998 |
| WO | WO 99/52548 | 10/1999 |
| WO | WO 00/15238 | 3/2000 |
| WO | WO 01/62283 | 8/2001 |
| WO | WO 01/68105 | 11/2001 |
| WO | WO 01/80807 | 11/2001 |
| WO | WO 02/058711 | 8/2002 |
| WO | WO 03/004507 | 1/2003 |
| WO | WO 03/054077 | 7/2003 |
| WO | WO 2004/014320 A3 | 2/2004 |
| WO | WO 2004/021994 A3 | 3/2004 |
| WO | WO 2004/030613 | 3/2004 |
| WO | WO2005/018544 * | 3/2005 |
| WO | WO 2005/027936 | 3/2005 |
| WO | WO 2005/027938 | 3/2005 |
| WO | WO 2005/049044 | 6/2005 |
| WO | WO 2005/070213 | 8/2005 |
| WO | WO 2005/113128 | 12/2005 |
| WO | WO 2006/007372 | 1/2006 |
| WO | WO 2006/032039 | 3/2006 |
| WO | WO 2006/085895 | 8/2006 |
| WO | WO 2006/119395 | 11/2006 |
| WO | WO 2007/050643 | 5/2007 |
| WO | WO 2007/063267 | 6/2007 |
| WO | WO 2007/063268 | 6/2007 |
| WO | WO 2007/084661 | 8/2007 |
| WO | WO 2007/109564 | 9/2007 |

OTHER PUBLICATIONS

Abstract of Urbaniak et al (British Journal of Haematology, 1980, vol. 46, pp. 447-453).*
Abstract of Michaelsen et al (Molecular Immunology, 1992, vol. 29, pp. 319-326).*
Jamas et al ('PGG Glucans' In: Polymeric Drugs and Drug Delivery Systems, ACS Symposium Series, 1991).*
Hong et al (Cancer Research, 2003, vol. 63, pp. 9023-9031).*
Yan et al (Expert Opinion in Biological Therapy, 2005, vol. 5, pp. 691-702).*
Supplementary Partial European Search Report, Feb. 5, 2008, for Sloan-Kettering Institute for Cancer Research, European Application No. EP 02 70 7502, filed Aug. 4, 2003.
PCT International Search Report, Sep. 26, 2007, for Sloan-Kettering Institute for Cancer Research, Int'l Application No. PCT/US07/01427, Filed Jan. 18, 2007.
PCT Written Opinion of the International Searching Authority, Sep. 26, 2007, for Sloan-Kettering Institute for Cancer Research, Int'l Application No. PCT/US07/01427, Filed Jan. 18, 2007.
Chinese Office Action, May 9, 2008, for Sloan-Kettering Institute for Cancer Research, Chinese Application No. 200480020356.6, Filed Jan. 16, 2006, corresponding to PCT/US04/23099.
U.S. Office Action, Feb. 22, 2008, for Nai-Kong V. Cheung, U.S. Appl. No. 10/565,484, filed Jan. 17, 2006.
U.S. Office Action, Aug. 7, 2007, for Nai-Kong V. Cheung, U.S. Appl. No. 11/218,044, filed Aug. 31, 2005.
U.S. Office Action, Aug. 7, 2007, for Nai-Kong V. Cheung, U.S. Appl. No. 10/621,027, filed Jul. 16, 2003.
U.S. Office Action, Jan. 4, 2007, for Nai-Kong V. Cheung, U.S. Appl. No. 10/621,027, filed Jul. 16, 2003.
U.S. Office Action, Nov. 22, 2006, for Nai-Kong V. Cheung, U.S. Appl. No. 11/218,044, filed Aug. 31, 2005.
U.S. Office Action, Mar. 10, 2006, for Nai-Kong V. Cheung, U.S. Appl. No. 11/218,044, filed Aug. 31, 2005.
U.S. Office Action, Mar. 6, 2006, for Nai-Kong V. Cheung, U.S. Appl. No. 10/621,027, filed Jul. 16, 2003.
U.S. Office Action, Jul. 13, 2005, for Nai-Kong V. Cheung, U.S. Appl. No. 10/621,027, filed Jul. 16, 2003.
U.S. Office Action, Dec. 17, 2004, for Nai-Kong V. Cheung, U.S. Appl. No. 10/621,027, filed Jul. 16, 2003.
Beta Glucan Health Center webpage, Nov. 10, 2000, "PLEURAN—Beta-1,3/1-6-Glucan," http://www.glucan.com/therapy/therapy.com.
1999 The Merck Manual of Diagnosis and Therapy, 397-398, 948-949, 1916, 1979-1981.
Adachi et al., 1990, "Macrophage Activation in Vitro by Chemically Cross-Linked (1-3)-β-D-Glucans", Chem. Pharm. Bull., 38(4):988-992.
Azuma, Ichiro, "Development of Immunostimulants in Japan", Immunostimulants: Now and Tomorrow, 41-56, 1987.
Bergman et al., 1999, "Treatment of Neoplastic Meningeal Xenografts by Intraventricular Administration of an Antiganglioside Monoclonal Antibody, 3F8," Int. J. Cancer, 82:538-548.
Bluhm et al., 1977, "The triple helical structure of lentinan, a linear β-(1→3)-D-glucan", Can J Chem, 55:293-299.
Bogwald et al., 1982, "The Cytoxic Effect of Mouse Macrophages Stimulated in Vitro by a β-1,3-D-Glucan from Yeast Cell Walls", Scandinavian Journal of Immunology, 15:297-304.
Bohn, J.A., and BeMiller, J.N., 1995, "(1→3)-β-Glucans as biological response modifiers: a review of structure-functional activity relationships," Carbohydrate Polymers, 28:3-14.
Bowers et al., 1989, "Glucan Enhances Survival in an Intraabdominal Infection Model", Journal of Surgical Research, vol. 47(2):183-188.
Capurro et al., 1998, "FC-2.15, a monoclonal antibody active against human breast cancer, specifically recognizes Lewisx hapten," Cancer Immunol. Immunother., 45:334-339.
Cheung, N.-K. V., et al., 2002, "Quantitation of GD2 Synthase mRNA by Real-Time Reverse Transcription-Polymerase Chain Reaction—Utility in Bone Marrow Purging of Neuroblastoma by Anti-GD2 Antibody 3F8," Cancer, 94:3042-3048.
Cheung, N.-K. V., et al., 1985, "Monoclonal Antibodies to a Glycolipid Antigen on Human Neuroblastoma Cells," Canc. Res., 45:2642-2649.
Chihara et al., 1970, "Fractionation and purification of the polysaccharides with Marked Antitumor Activity, Especially Lentinan, from *Lentinus edodes* (Berk.) Sing. (an Edible Mushroom)", Cancer Res, 30:2776-2781.
Chihara et al., 1981, "The antitumor polysaccharide Lentinan: an overview", Manipulation of Host Defence Mechanisms, 1-16.
Chihara et al., 1982, "Current Status and Perspectives of Immunomodulators of Microbial Origin", International Journal of Tissue Reactions, 4:207-225.
Damge et al., 1996, "Intestinal absorption of PLAGA microspheres in the rat," J. Anat., 189:491-501.

D'Amico et al., 2000, "Molecular Biologic Substaging of Stage I Lung Cancer According to Gender and Histology," Ann. Thorac. Surg., 69:882-886.

David et al., 1996, "Growth arrest of solid human neuroblastoma xenografts in nude rats by natural IgM from healthy humans," Nature Medicine, 2:686-689.

Di Luzio et al., 1985, "Glucans as Immunomodulators", Advances in Immunopharmacology, Permagon Press. NY, 369-375.

Di Luzio et al., 1980, "Comparative Evaluation of the Tumor Inhibitory and Antibacterial Activity of Solubilized and Particulate Glucan", Recent Results in Cancer Research, 75:165-172.

Di Luzio, Nicholas R., 1985, "Update on the Immunomodulating Activities of Glucans", Springer Seminars in Immunopathology, 8:387-400.

Di Luzio, Nicholas R., 2003, "Immunopharmacology of glucan: a broad spectrum enhancer of host defense mechanisms", T.I.P.S., 344-347.

Engler et al., 2001, "A Novel Metastatic Animal Model Reflecting the Clinical Appearance of Human Neuroblastoma: Growth Arrest of Orthotopic Tumors by Natural, Cytotoxic Human Immunoglobulin M Antibodies," Cancer Research 61:2968-2973.

Florence A., 1997, "The oral absorption of micro- and nanoparticulates: Neither exceptional nor unusual," Pharmaceutical Research, 14(3):259-266.

Hamuro et al., 1971, "The significance of the higher structure of the polysaccharides lentinan and pachymaran with regard to their antitumour activity", Chem. Biol. Interactions, 3:69-71.

Hamuro et al., 1978, "Solid phase activation of alternative pathway of complement by β-1,3-glucans and its possible role for tumour regressing activity", Immunology, 34:695-705.

Harada et al., 1997, "Oral Administration of PSK can Improve the Impaired Anti-Tumor CD4+ T-Cell Response in Gut-Associated Lymphoid Tissue (GALT) of Specific-Pathogen-Free Mice," Int. J. Cancer, 70:362-372.

Hellstrom, I. et al., 1986, "Antitumor effects of L6, and IgG2a antibody that reacts with most human carcinomas," Proc. Natl. Acad. Sci. USA, 83:7059-7063.

Herre et al., 2004, "Dectin-1 and its role in the recognition of β-glucans by macrophages," Mol. Immunol. 40 (12):869-876.

Herrera et al., 2000, "Immunotoxins against CD19 and CD22 are effective in killing precursor-B acute lymphoblastic leukemia cells in vitro," Leukemia, 14:853-858.

Jamas et al., 1990, "Spectral Analysis of Glucan Produced by Wild-Type and Mutant *Saccharomyces cerevisiae*", Carbohydrate Polymers, 13:207-219.

Jani et al., 1990, "Nanoparticle uptake by the rat gastrointestinal mucosa: quantitation and particle size dependency," J. Pharm. Pharmacol., 42:821-826.

Kim, Y.-S., et al., 2000, "Gram-negative Bacteria-binding Protein, a Pattern Recognition Receptor for Lipopolysaccharide and β-1,3-Glucan That Mediates the Signaling for the Induction of Innate Immune Genes in *Drosophila melanogaster* Cells," J. Biol. Chem., 275(42):32721-32727.

Kirby et al., 1981, "Oat-bran intake selectively lowers serum low-density lipoprotein cholesterol concentrations of hypercholesterolemic men", American Journal of Clinical Nutrition, 34:824-829.

Komatsu et al., 1975, "Influence of Schizophyllan, Streptomycin and Rifampicin on Histopathological changes in mice infected with Tubercle Bacilli", Japanese Journal of Antibiotics, XXVII(4):549-557. (English abstract included).

Kotera, Y., et al., 1994, "Humoral Immunity against a Tandem Repeat Epitope of Human Mucin MUC-1 in Sera from Breast, Pancreatic, and Colon Cancer Patients," Cancer Res., 54:2856-2860.

Maeda et al., 1971, "Lentinan, a new immune-accelerator of cell-mediated responses", Nature, 229:634.

Maloney et al., 1997, "IDEC-C2B8 (Rituximab) Anti-CD20 Monoclonal Antibody Therapy in Patients With Relapsed Low-Grade Non-Hodgkin's Lymphoma," Blood, 90(6):2188-2195.

Matzinger, P., 1994, "Tolerance, Danger, and the Extended Family," Annu. Rev. Immunol., 12:991-1045.

Mendelsohn et al., 1988, "Monoclonal Antibodies Against the Receptor for Epidermal Growth Factor as Potential Anticancer Agents," Cellular and Molecular Biology of Tumors and Potential Clinical Applications, 307-312.

Mendelsohn, J., 1997, "Epidermal Growth Factor Receptor Inhibition by a Monoclonal Antibody as Anticancer Therapy," Clin. Cancer Res., 3:2703-2707.

Hiroaki Nanba and Keiko Kubo, 1997; "Effect of Maitake D-Fraction on Cancer Prevention," Annal. N.Y. Acad. Sci. 833:204-207.

Ohno et al., 2000, "Antitumor 1,3-β-Glucan from Cultured Fruit Body of *Sparassis crispa*," Biol. Pharm, Bull., 23(7):866-872.

Ollert et al., 1996, "Normal human serum contains a natural IgM antibody cytotoxic for human neuroblastoma cells," Proc. Natl. Acad. Sci. USA, 93:4498-4503.

Ollert et al., 1997, "Mechanisms of in vivo antineuroblastoma activity of human natural IgM," European Journal of Cancer, 33(12)1942-1948.

Onizuka et al., 1999, "Tumor Rejected by in Vivo Administration of Anti-CD25 (Interleukin-2 Receptor α) Monoclonal Antibody," Cancer Research, 59:3128-3133.

Oxford Textbook of Oncology, 1995, "Chemotherapy: General Aspects", Peckham, Pinedo and Veronesi, ed., vol. 1, 447-453.

Patchen et al., 1984, "Soluble Polyglycans Enhance Recovery from Cobalt-60-Induced Hemopoietic Injury", Journal of Biological Response Modifiers, 3:627-633.

Peat et al., 1958, "Polysaccharides of Baker's Yeast. Part II. Yeast Glucan", Journal Chem. Soc. Part 1, 3862-3868.

Rai, K.R. and Gupta, N., 2000, "Monoclonal Antibodies in Chronic Lymphocytic Leukemia," Rev. Clin. Exp. Hematol., 4.2:134-144.

Ren et al., 1997, "Mechanisms of Anti-Lung Cancer Activity for Monoclonal Antibody to Epidermal Growth Factor Receptor," Disi Junyi Daxue Xuebao, 18(6):560-562 (abstract only).

Robbins et al., 1977, "Cholesterol Lowering Effect of Dietary Yeast and Yeast Fractions", Journal of Food Science, 42 (3):694-698.

Saito et al., 1977, "A C-N.M.R.-spectral study of a gel forming, branched (1→3)-β-D-Glucan, (Lentinan) from *Lentinus edodes*, and its acid-degraded fractions. Structure, and Dependence of Confirmation on the Molecular Weight", Carbohydrate Research, 58:293-305.

Sasaki et al., 1976, "Antitumor Activity of Degraded Products of Lentinan: it's Correlation with Molecular Weight", Gann, 67:191-195.

Seljelid et al., 1977, "Glycan Stimulation of Macrophages in Vitro", Experimental Cell Research, 131:121-129.

Seljelid et al., 1986, "A water soluble aminated β-1,3-D-glucose derivative caused regression of solid tumors in mice", Bioscience Reports 6:845-852.

Singh et al., 1974, "Scleroglucan, an antitumor polysaccharide from *Sclerotium glucanicum*", Carbohydrate Research, 37:245-247.

Slovin, S.F. et. al., 1999, "Carbohydrate vaccines in cancer: Immunogenicity of a fully synthetic globo H hexasaccharide conjugate in man," Proc. Natl. Acad. Sci. USA, 96:5710-5715.

Soiffer et al., 1997, "Administration of R24 Monoclonal Antibody and Low-Dose Interleukin 2 for Malignant Melanoma," Clinical Cancer Research, 3:17-24.

Song et al., "Yeast glucan and immunotherapy of infectious diseases", chapter 18, 533-545, In: Lysosomes in Applied Biology, Dingle et al Ed.s, Amsterdam, 1979.

Williams et al., 1991, "Development, physicochemical characterization and preclinical efficacy evaluation of a water soluble glucan sulfate derived from *Saccharomyces cerevisiae*," Immunopharmacology 22:139-155.

Zimmerman, J.W., et al., 1998, "A Novel Carbohydrate-Glycosphingolipid Interaction between a β-(1~3)-Glucan Immunomodulator, PGG-glucan, and Lactosyceramide of Human Leukocytes," J. Biol. Chem., 273(34):22014-22020.

PCT International Preliminary Examination Report, Mar. 27, 2003, Sloan-Kettering Institute for Cancer Research, Int'l Application No. PCT/US02/01276, Filed Jan. 15, 2002.

PCT International Search Report, Feb. 28, 2005, Sloan-Kettering Institute for Cancer Research, Int'l Application No. PCT/US04/23099, Filed Jul. 16, 2004.

PCT International Search Report, Apr. 14, 2005, Sloan-Kettering Institute for Cancer Research, Int'l Application No. PCT/US04/23099, Filed Jul. 16, 2004.

PCT Written Opinion of the International Searching Authority, Apr. 14, 2005, Sloan-Kettering Institute for Cancer Research, Int'l Application No. PCT/US04/23099, Filed Jul. 16, 2004.

PCT International Search Report, Jun. 5, 2002, Sloan-Kettering Institute for Cancer Research, Int'l Application No. PCT/US02/01276, Filed Jan. 15, 2002.

PCT Written Opinion, Nov. 25, 2002, Sloan-Kettering Institute Cancer Research, et al, Int'l Application No. PCT/US02/01276, Filed Jan. 15, 2002.

PCT International Preliminary Report on Patentability, Jan. 26, 2006, Sloan-Kettering Institute for Cancer Research, et al., Int'l Application No. PCT/US2004/023099, Filed Jul. 16, 2004.

PCT Corrected Written Opinion of the International Searching Authority, Aug. 10, 2005, Sloan-Kettering Institute for Cancer Research, et al, Int'l Application No. PCT/US04/23099, Filed Jul. 16, 2004.

PCT Corrected International Search Report, Aug. 10, 2005, Sloan-Kettering Institute for Cancer Research, et al, Int'l Application No. PCT/US2004/23099, Filed Jul. 16, 2004.

Search Report prepared by the Norwegian Patent Office, dated May 4, 2005.

Allendorf et al., 2004, "Macrophages shuttle orally administered β-glucan to potentiate the CR3-dependent tumoricidal effects of monoclonal antibodies in mouse tumor models", FASEB Journal, vol. 17, No. 7, C128.

Arturson, G. et al., 1966, "Intravascular Persistence and Renal Clearance of Dextran of Different Molecular Sizes in Normal Children", Arch. Dis. Childh., vol. 41, 168-172.

Arturson, G. and Wallenius, G., 1964, "The Renal Clearance of Dextran of Different Molecular Sizes in Normal Humans", Scandinaz J. Clin & Lab Investigation, vol. 1, 81-86.

Babineau, T. et al., 1994, "A Phase II Multicenter, Double-blind, Randomized, Placebo-Controlled Study of Three Dosages of an Immunomodulator (PGG-Glucan) in High-Risk Surgical Patients", Arch. Surg., vol. 129, 1204-1210.

Babineau, T. et al., 1994, "Randomized Phase I/II Trial of a Macrophage-Specific Immunomodulator (PGG-Glucan) in High-Risk Surgical Patients", Annals of Surgery, vol. 220, No. 5, 601-609.

Cheung, N. and Modak, S., 2002, "Oral (1→3),(1→4)-β-D-Glucan Synergizes with Antiganglioside GD2 Monoclonal Antibody 3F8 in the Therapy of Neuroblastoma", Clinical Cancer Research, vol. 8, 1217-1223.

Cheung, N.K. et al., 2002, "Orally administered β-glucans enhance anti-tumor effects of monoclonal antibodies", Cancer Immunol Immunother. 51(10):557-564.

Chihara, G. et al., 1987, "Antitumor and Metastasis-Inhibitory Activities of Lentinan as an Immunomodulator: An Overview", Cancer Detection and Prevention Supplement vol. 1, 423-443.

Dellinger, E. et al., 1999, "Effect of Pog-glucan on the Rate of Serious Postoperative Infection or Death Observed After High Risk Gastrointestinal Operations", Arch. Surg., vol. 134, 977-983.

Hanaue, H. et al., 1989, "Basic Studies on Oral Administration of Lentinan (I)", J. Jpn. Soc. Cancer Ther., vol. 8, 1566-1571.

Hanaue, H. et al., 1989, "Effects of oral lentinan on T-cell Subsets in Peripheral Venous Blood", Clin. Ther. 11:614-622.

Hayakawa, K. et al., 1993, "Effect of Krestin (PSK) as Adjuvant Treatment on the Prognosis after Radical Radiotherapy in Patients with Non-small Cell Lung Cancer". Anticancer Res. 13:1815-1820.

Hong et al., "Mechanism by Which Orally Administered β-1,3-Glucans Enhance the Tumoricidal Activity of Antitumor Monoclonal Antibodies in Murine Tumor Models", The Journal of Immunology, vol. 173, No. 5, pp. 797-806 (2004).

Hotta, H. et al., 1993, "Augmentation of protective immune responses against Sendai virus infection by fungal polysaccharide schizophyllan", Int, J. Immunopharmacol. 15:55-60.

Morinaga, H. et al., 1994, "An in vivo study of hepatic and splenic interleukin-1β mRNA expression following oral PSK or LEM administration", Gann 85:1298-1303.

Nanba, H. et al., 1995, "Activity of Maitake D-faction to Inhibit Carcinogensis and Metastasis", Ann. N. Y. Acad. Sci. 768:243-245.

Nanba, H. and H. Kuroda, 1987, "Antitumor Mechanisms of Orally Administered Shiitake Fruit Bodies", Chem. Pharm. Bull. (Tokyo) 35:2459-2464.

Nanba, H. and H. Kuroda, 1988, "Potentiation of Host-Mediated Antitumor Activity by Orally Administered Mushroom (*Agaricus bispora*) Fruit Bodies", Chem, Pharm. Bull. (Tokyo) 36:1437-1444.

Hishida, I. et al., 1988, "Antitumor Activity Exhibited by Orally Administered Extract from Fruit Body of *Grifola frondosa* (Maitake)", Chem. Pharm. Bull (Tokyo) 36:1819-1827.

Kidd, P., 2000, "The Use of Mushroom Glucans and Proteoglycans in Cancer Treatment", Alternative Medicine Review, vol. 5, No. 1, 4-27.

Mayer, L. and Shao, L., 2004, "Therapeutic Potential of Oral Tolerance", Nature Reviews Immunology, vol. 4, 407-419.

Mehvar, R., 2003, "Recent Trends in the Use of Polysaccharides for Improved Delivery of Therapeutic Agents: Pharmacokinetic and Pharmacodynamic Perspectives", Current Pharmaceutical Biotechnology, vol. 4, 283-302.

Nanba, H. et al., 1987, "Antitumor action of shiitake (*Lentinus edodes*) fruit bodies orally administered to mice". Chem. Pharm. Bull. (Tokyo) 35:2453-2458.

Ohmori, T. et al., 1988, "Dissociation of a Glucan Fraction (CO-1) from Protein-bound Polysaccharide of *Cordyceps ophioglossides* and Analysis of its Antitumor Effect", Chem. Pharm. Bull. (Tokyo) 36:4512-4518.

Ostroff et al., 2003, "Immune-Enhancing Effects of Oral Yeast β 1,3/1,6 Glucans", American Chemical Society, vol. 225, No. 1-2, pp. AGFD 8.

Papila et al., 2004, "The Effect of Oral β-glucan in Addition to Systemic Chemotherapy on the Leukocyte Values and Oral Mucositis in the Patients with Head-neck Tumors", International Review of Allergology & Clinical Immunology, vol. 10, No. 2, 59-61.

Ross, et al., 1999, "Therapeutic intervention with complement and β-glucan in cancer", Immunopharmacology 42, 61-74.

Sakurai, T. et al., 1992, "Enhancement of Murine Alveolar Macrophage Functions by Orally Administered β-glucan", Int. J. Immunopharmacol. 14:821-830.

Shimazu, H. et al., 1980, "Intravenous chronic toxicity of lentinan in rats: 6-month treatment and 3-month recovery (author transl.)", National Library of Medicine (PubMed), J Toxicol Sci., 33-57.

Sortwell, R. et al., 1981, "Chronic Intravenous Administration of Lentinan to the Rhesus Monkey", Toxicology Letters, vol. 9, 81-85.

Suzuki, et al., 1990, "Effect of orally administered β-glucan on macrophage function in mice". Int. J. Immunopharmacology 12:6, 676-684.

Suzuki, M. et al., 1994, "Antitumor and Immunological Activity of Lentinan in Comparison with LPS", International Society for Immunopharmacology, pp. 463-468.

Suzuki, I. et al., 1989, "Immunomodulation by Orally Administered β-glucan in Mice". Int. J. Immunopharmacol. 11:761-769.

Suzuki, I. et al., 1991, "Inhibition of Experimental Pulmonary Metastasis of Lewis Lung Carcinoma by Orally Administered β-glucan in Mice", Chem. Pharm. Bull. (Tokyo) 39:1606-1608.

Tsukagoshi, S. et al., 1984, "Krestin (PSK)", Cancer Treat. Rev. 11:131-155.

Vetvicka, et al. 2002, "Pilot Study: Orally-administered Yeast Beta 1,3-glucan Prophylactically protects against anthrax infection and cancer in mice". Journ. Ameri. Nutraceutical Assoc., vol. 5:2.

Vetvicka, V. et al., 1996, "Soluble β-Glucan Polysaccharide Binding to the Lectin Site of Neutrophil or Natural Killer Cell Complement Receptor Type3 (CD11b/CD18) Generates a Primed State of the Receptor Capable of Mediating Cytotoxicity of iC3b-Opsonized Target Cells". J. Clin. Invest., 98:50-61.

Xia, Y. et al., 1999, "The β-Glucan-Binding Lectin Site of Mouse CR3 (CD11b1CD18) and Its Function in Generating a Primed State of the Receptor That Mediates Cytotoxic Activation in Response to iC3b-Opsonized Target Cells". J. Immunology, 162:2281-2290.

Yan, J. et al., 1999, "β-Glucan, a "Specific" Biologic Response Modifier That Uses Antibodies to Target Tumors for Cytotoxic Recognition by Leukocyte Complement receptor Type 3 (CD11b/CD18)". The Journal of Immunology, 163:3045-3052.

Basic and Clinical Pharmacology, 1998, 7th edition, Bertram G. Katzung, pp. 881-884.

U.S. Office Action, Mar. 5, 2008, for Nai-Kong V. Cheung, U.S. Appl. No. 11/334,763, filed Jan. 17, 2006.

U.S. Office Action, Dec. 17, 2008, for Nai-Kong V. Cheung, U.S. Appl. No. 10/565,484, filed Jan. 17, 2006.

Chinese Office Action, Oct. 31, 2008, for Sloan-Kettering Institute for Cancer Research, Chinese Application No. 200480020356.6, Filed Jan. 16, 2006, corresponding to PCT/US04/23099.

Australian Office Action, Dec. 4, 2008. for Sloan-Kettering Institute for Cancer Research, Australian Application No. 2008207369, Filed Aug. 18, 2008, continuation-in-part of PCT/US07/01427.

Chan et al., 2007, "Response of human dendritic cells to different immunomodulatory polysaccharides derived from mushroom and barley", International Immunology, 19(7): 891-899.

Cheung et al., 1994, "Antibody response to murine anti-GD2 monoclonal antibodies: correlation with patient survival", Cancer research, 54(8): 2228-2233.

Cheung et al., 2006, "FCGR2A polymorphism is correlated with clinical outcome after immunotherapy of neuroblastoma with anti-GD2 antibody and granulocyte macrophage colony-stimulating factor", J. Clinical Oncology, 24(18): 2885-2890.

Dhodapkar et al., 2002, "Antitumor monoclonal antibodies enhance cross-presentation ofcCellular antigens and the generation of myeloma-specific killer T cells by dendritic cells", J. Experimental Medicine, 195(1): 125-133.

Diaz De Stahl et al., 2003, "A role for complement in feedback enhancement of antibody responses by IgG3", J. Experimental Medicine, 197(9): 1183-1190.

Hong et al., 2003, "Beta-glucan functions as an adjuvant for monoclonal antibody immunotherapy by recruiting tumoricidal granulocytes as killer cells", Cancer research, 63(24): 9023-9031.

Imai et al., 2005, "Complement-mediated mechanisms in anti-GD2 monoclonal antibody therapy of murine metastatic cancer", Cancer Research, 65(22): 10562-10568.

Kushner et al., 2001, "Phase II trial of the anti-G(D2) monoclonal antibody 3F8 and granulocyte-macrophage colony-stimulating factor for neuroblastoma", J. Clin. Oncol., 19(22): 4189-94.

Yoshitomi et al., 2005, "A role for fungal {beta}-glucans and their receptor Dectin-1 in the induction of autoimmune arthritis in genetically susceptible mice", J. Experimental Medicine, 201(6): 949-960.

Zhang et al., 1998, "Antibodies against GD2 ganglioside can eradicate syngeneic cancer micrometastases", Cancer Research, 58(13): 2844-2849.

U.S. Office Action, Oct. 24, 2008, for Nai-Kong V. Cheung, U.S. Appl. No. 12/036,462, filed Feb. 25, 2008.

U.S. Office Action, Oct. 22, 2008, for Nai-Kong V. Cheung, U.S. Appl. No. 11/334,763, filed Jan. 17, 2006.

Allendorf et al., 2005, "C5a-Mediated Leukotriene B4-Amplified Neutrophil Chemotaxis Is Essential in Tumor Immunotherapy Facilitated by Anti-Tumor Monoclonal Antibody and β-Glucan", The Journal of Immunology, 174:7050-7056.

Gelderman et al., 2004, "Complement function in mAb-mediated cancer immunotherapy", TRENDS in Immunology, 25(3):158-164.

Li et al., 2007, "Combined Yeast β-Glucan and Antitumor Monoclonal Antibody Therapy Requires C5a-Mediated Neutrophil Chemotaxis via Regulation of Decay-Accelerating Factor CD55", Cancer Research, 67;7421-7430.

Yan et al., 2005, "Yeast whole glucan particle β-glucan in conjunction with antitumour monoclonal antibodies to treat cancer", Expert Opinion on Biological Therapy, 5(5):691-702.

Indian First Examination Report, Feb. 12, 2009, for Nai-Kong V. Cheung, Indian Application No. 186/MUM/NP/2006, Filed Feb. 15, 2006.

Chinese Office Action, Feb. 27, 2009, for Sloan-Kettering Institute for Cancer Research, Chinese Application No. 200480020356.6, Filed Jan. 16, 2006, corresponding to PCT/US04/23099.

Supplementary European Search Report, Jan. 26, 2010, for Sloan-Kettering Institute for Cancer Research, European Application No. EP 07718218, filed Jul. 16, 2008, National stage of Int'l Application No. PCT/US07/01427, Filed Jan. 17, 2007.

Canadian Office Action, Jan. 25, 2010, for Sloan-Kettering Institute for Cancer Research, Canadian Application No. 2,434,938, Filed Jul. 15, 2003, National Stage of PCT/US02/01276, Filed Jan. 15, 2002.

Canadian Office Action, May 31, 2010, for Sloan-Kettering Institute for Cancer Research, Canadian Application No. 2,536,632, Filed Jan. 13, 2006, National Stage of PCT/US04/23099, Filed Jul. 16, 2004.

Canadian Office Action, Dec. 6, 2010, for Sloan-Kettering Institute for Cancer Research, Canadian Application No. 2,434,938, Filed Jul. 15, 2003, National Stage of PCT/US02/01276, Filed Jan. 15, 2002.

Chinese Office Action, Aug. 27, 2010, for Sloan-Kettering Institute for Cancer Research, Chinese Application No. 2007800075400, Filed Sep. 2, 2008, National Stage of PCT/US07/01427, Filed Jan. 17, 2007.

European Office Action, Apr. 6, 2010, for Sloan-Kettering Institute for Cancer Research, European Application No. 04786081.2, Filed Apr. 18, 2006, National Stage of PCT/US04/23099, Filed Jul. 16, 2004.

European Office Action, May 27, 2010, for Sloan-Kettering Institute for Cancer Research, European Application No. 07718218.6, Filed Aug. 17, 2008, National Stage of PCT/US07/01427, Filed Jan. 17, 2007.

European Office Action, Jan. 25, 2011, for Sloan-Kettering Institute for Cancer Research, European Application No. 02 707 502.7, Filed Aug. 4, 2003, National Stage of PCT/US02/01276, filed on Jan. 15, 2002.

Japanese Office Action, Jan. 7, 2011, for Sloan-Kettering Institute for Cancer Research, Japanese Application No. 2006-520398, Filed Jan. 16, 2006, National Stage of Int'l App'l No. PCT/US04/23099, Filed Jul. 16, 2004.

Japanese Office Action, May 6, 2011, for Sloan-Kettering Institute for Cancer Research, Japanese Application No. 2006-520398, Filed Jan. 16, 2006, National Stage of Int'l App'l No. PCT/US04/23099, Filed Jul. 16, 2004.

Korean Office Action, Apr. 12, 2011, for Sloan-Kettering Institute for Cancer Research, Korean Application No. 10-2006-7000839, Filed Jan. 13, 2006, National Stage of PCT/US04/23099, Filed Jul. 16, 2004.

Mexican Office Action, Mar. 25, 2010, for Sloan-Kettering Institute for Cancer Research, Mexican Application No. PA/a/2006/000615, Filed Jan. 16, 2006, National Stage of Int'l App'l No. PCT/US04/23099, Filed Jul. 16, 2004.

U.S. Office Action, May 6, 2010, for Nai-Kong V. Cheung, U.S. Appl. No. 11/334,763, filed Jan. 17, 2006.

U.S. Office Action, May 25, 2010, for Rolf Einar Engstad, U.S. Appl. No. 12/161,285, filed Jul. 17, 2008.

U.S. Advisory Action, Jul. 22, 2010, for Nai-Kong V. Cheung and Rolf Einar Engstad, U.S. Appl. No. 12/212,352, filed Sep. 17, 2008.

Böhm, Nicolai and Kulicke, Werner-Michael, 1999, "Rheological studies of barley (1->3)(1->4)-β-glucan in concentrated solution: mechanistic and kinetic investigation of the gel formation", Carbohydrate Research, 315:302-311.

Chen, J. and Seviour, R., 2007, "Medicinal importance of fungal beta-(1→3), (1→6)-glucans", Mycological Research, 111(Pt 6):635-52.

Pelley, R.P. and Strickland, F.M., 2000, "Plants, polysaccharides, and the treatment and prevention of neoplasia", Critical Reviews in Oncogenesis, 11(3-4):189-225.

Penna et al., 1996, "Pulmonary Metastases Neutralization and Tumor Rejection by In Vivo Administration of Beta Glucan and Bispecific Antibody", International Journal of Cancer, 65:377-382.

Wilson et al., 2004, "Reduced and High Molecular Weight Barly β-Glucans Decrease Plasma Total and Non-HDL-Cholesterol in Hypercholesterolemic Syrian Golden Hamsters", Journal of Nutrition, vol. 134, pp. 2617-2622.

Chinese Office Action, Nov. 2, 2011, for Sloan-Kettering Institute for Cancer Research, Chinese Application No. 2007800075400, Filed Sep. 2, 2008, National Stage of Int'l App'l No. PCT/US07/01427, Filed Jan. 17, 2007.

Japanese Office Action, Aug. 26, 2011, for Sloan-Kettering Institute for Cancer Research, Japanese Application No. 2006-520398, Filed Jan. 16, 2006, National Stage of Int'l App'l No. PCT/US04/23099, Filed Jul. 16, 2004.

U.S. Office Action, Sep. 27, 2011, for Nai-Kong V. Cheung and Rolf Einar Engstad, U.S. Appl. No. 12/212,352, filed Sep. 17, 2008.

Beum et al., 2004, "Complement activation and C3b deposition on rituximab-opsonized cells substantially blocks binding of phycoerythrin-labeled anti-mouse IgG probes to rituximab", Journal of Immunological Methods, 294: 37-42.

Chan et al., Nov. 2005, "Immunopotent polysaccharides of different sources selectively activate human dendritic cells", Blood, 106(2):49B (abstract).

Schultes, Birgit C. and Nicodemus, Christopher F., 2004, "Using Antibodies in tumour immunotherapy", Expert Opinion on Biological Therapy, 4:1265-1284.

Hazama et al., 2009, "Efficacy of Orally Administered Superfine Dispersed Lentinan (β-1,3-Glucan) for the Treatment of Advanced Colorectal Cancer", AntiCancer Research, 29: 2611-2618.

Hsu et al., 2002, "CCTLA4 Blockade Maximizes Antitumor T-Cell Activation by Dendritic Cells Presenting Idiotype Protein or Opsonized Anti-CD20 Antibody-Coated Lymphoma Cells", Journal of Immunotherapy, 25 (6): 455-468.

Jamas et al., 1991, "PGG-Glucans: A Novel Class of Macrophage-Activating Immunomodulators", Chapter 5 in Polymeric Drugs and Drug Delivery Systems: Dunn, R., et al.; pp. 44-51; ACS Symposium Series; American Chemical Society: Washington, D.C.

Onrust et al., 1999, "Rituximab", Drugs, 58(1):79-88; discussion 89-90.

Canadian Office Action, Jan. 27, 2012, for Sloan-Kettering Institute for Cancer Research and Biotec Pharmacon ASA, Canadian Application No. 2,637,205, Filed Jul. 15, 2008.

U.S. Office Action, Mar. 7, 2012, for Nai-Kong V. Cheung and Rolf Einar Engstad, U.S. Appl. No. 12/212,352, filed Sep. 17, 2008.

U.S. Office Action, May 22, 2012, for Nai-Kong V. Cheung, U.S. Appl. No. 12/854,603, filed Aug. 11, 2010.

U.S. Office Action, May 29, 2012, for Nai-Kong V. Cheung, U.S. Appl. No. 12/767,237, filed Apr. 26, 2010.

Australian Office Action. Oct. 27. 2009. For Sloan-Kettering Institute for Cancer Research, Australian Application No. 2008207369, Aug. 18, 2008, continuation-in-part of PCT/US07/01427, Filed Jan. 17, 2007.

Australian Office Action. Jun. 12, 2009. For Sloan-Kettering Institute for Cancer Research, Australian Application No. 2008207369, Filed Aug. 18, 2008, continuation-in-part of PCT/US07/01427, Filed Jan. 17, 2007.

Canadian Office Action, Mar. 26, 2009, for Sloan-Kettering Institute for Cancer Research, Canadian Application No. 2,434,938, Filed Jul. 15, 2003, National Stage of PCT/US02/01276, Filed Jan. 15, 2002.

Canadian Office Action, Oct. 29, 2009, for Sloan-Kettering Institute for Cancer Research, Canadian Application No, 2,536,632. Filed Jan. 13, 2006, National Stage of PCT/US04/23099, Filed Jul. 16, 2004.

Chinese Office Action. Jul. 24, for Sloan-Kettering Institute for Cancer Research, Chinese Application No. 200480020356.6, Filed Jan. 16, 2006, corresponding to PCT/US04/23099, Filed Jul. 16. 2004.

European Office Action, Mar. 30, 2009, for Sloan-Kettering Institute for Cancer Research. European Application No. 02 707 502.7, Filed Aug. 4, 2003, National Stage of PCT/US02/01276, Filed Jan. 15, 2002.

European Office Action, Oct. 21, 2009, for Sloan-Kettering Institute for Cancer Research, European Application No. 02 707 502.7, Filed Aug. 4, 2003, National Stage of PCT/US02/01276, Filed Jan. 15, 2002.

Mexican Office Action, Sep. 18, 2009, for Sloan-Kettering Institute for Cancer Research, Mexican Application No. PA/a/2006/000615, Filed Jan. 16, 2006, National Stage of PCT/US04123099. Filed Jul. 16, 2004. (with English translation).

Mexican Office Action: May 29, 2009, for Sloan-Kettering Institute for Cancer Research. Mexican Application No. Pa/a/2006/000615, Filed Jul. 16, 2004: corresponding to PCT/US04/23099, Filed Jul. 16, 2004.

U.S. Office Action, Aug. 11, 2008, for Nai-Kong V. Cheung, U.S. Appl. No. 10/565,484, Filed Jan. 17, 2006.

U.S. Office Action, Jun. 16, 2009, for Nai-Kong V. Cheung: U.S. Appl. No. 10/565,484, Filed Jan. 17, 2006.

U.S. Office Action, Jun. 2, 2009: for Nai-Kong V. Cheung, U.S. Appl. No. 11/334,763, Filed Jan. 17, 2006.

U.S. Office Action, Apr. 17, 2009, for Nai-Kong V. Cheung, U.S. Appl. No. 12/036,462, Filed Feb. 25, 2008.

U.S. Advisory Action, Aug. 6, 2009. For Nai-Kong V. Cheung, U.S. Appl. No. 12/036,462, Filed Feb. 26, 2008.

U.S. Advisory Action. Jul. 10, 2009: for Nai-Kong V. Cheung: U.S. Appl. No. 12/036,462, Filed Feb. 25, 2008.

U.S. Office Action, Nov. 12, 2009. For Nai-Kong V. Cheung, U.S. Appl. No. 12/212,352, Filed Sep. 17, 2008.

Breivik at al., 2005, "Soluble β-1,3/1,6-glucen from yeast inhibits experimental periodontal disease in Wistar rats", Journal Clinical Periodontol, 32(4):347-352. (abstract only).

Engstad et al., 2002, "The effect of soluble β-1,3-glucan and lipopolysaccharide on cytokine production and coagulation activation in whole blood", International Immunopharmacology, 2(11):1585-1597. (abstract only).

Chinese Rejection Decision, Jan. 29: for Sloan-Kettering Institute for Cancer Research. Chinese Application No. 200480020356.6, Filed Jan. 16, 2006. corresponding to PCT/US04/23099. Filed Jul. 16. 2004 (with English translation).

U.S. Office Action, Dec. 29, 2009, for Nai-Kong V. Cheung, U.S. Appl. No. 11/334,763, Filed Jan. 17, 2006.

Supplementary European Search Report, Dec. 11, 2009, for Sloan-Kettering Institute for Cancer Research, European Application No. EP 04786081.

Andoh, T., 1992, "Effects of Pervenous Administration of Lentinan and Concomitant Perendoscopic Localized Injection on Gastric Carcinoma in Elderly Patients", Nichidai Igaku Zasshi, 51(6):587-596. (abstract only).

Grobhans, Helge, 2000. "Gene Therapy—when a simple concept meets a complex reality", Funct Integr Genomics, 1:142-145.

Hamuro, Junji, 2005, "Anticancer Immunotherapy with perorally effective Lentinan", Cancer and Chemotherapy. 32(8):1209-1215. (abstract only).

Herlyn et al., 1985, Stimulation of monoclonal antibody-dependent macrophage-mediated cytotoxicity against human tumors by lentinan, International Journal of Immunopharmacology, 7(3):332. (abstract only).

Kaneko at at., 1989, Activity of Lentinan against Cancer and AIDS, International Journal of Immunotherapy, 5 (4):203-213.

Robertson of at., 1994, "β Glucans as Immunostiniulants in Fish", Modulators of Fish Immune Response, 1:83-99.

Sano et al.. 2002, "Antitumor Effects induced by the Combination of TNP-470 as an Angiogenesis Inhibitor and Lentinan as a Biological Response Modifier in a Rabbit Spontaneous Liver Metastasis Model", Surgery Today. 32:503-509.

Shiio et al., 1977, "A study of the condition of additive use of immunotherapeutic agent, Lentinan, and chemotherapeutic agent, cyclophosphamide", Journal of Japan Society for Cancer Therapy, 15:436. (abstract only).

Takita et al., 1998, "Successful treatment of hepatic metastasis of gastric cancer with 5'-DFUR and Lentinan", Cancer and Chemotherapy, 25(1):129-133, (abstract only).

* cited by examiner

Figure 5 n≥0 ; R= H or (C$_6$H$_{8-10}$O$_5$)$_m$; m (R1 + R2)=35 to 2000

THERAPY-ENHANCING GLUCAN

This application is the National Stage of International Application No. PCT/US2007/001427, filed Jan. 17, 2007, which is a Continuation-In-Part of U.S. Ser. No. 11/334,763, filed Jan. 17, 2006, which is hereby incorporated in its entirety by reference into this application.

Throughout this application, various references are cited. Disclosures of these publications in their entireties are hereby incorporated by reference into this application to more fully describe the state of the art to which this invention pertains.

BACKGROUND OF THE INVENTION

Glucans are a heterogeneous group of glucose polymers found in the cell walls of plants, bacteria and fungi. The basic structure of branched glucan consists of a linear backbone of β-1,3-linked glucose with β-1,6-linked side branches of β-1,3-glucan. β-1,3-glucan is the component responsible for the majority of biological activities of zymosan, a commonly used leukocyte stimulant derived from the cell wall of Bakers yeast (*Saccharomyces cerevisiae*).

Beta-glucans have been tested for tumor therapy in mice for nearly 40 years[1,2]. Several forms of mushroom-derived beta-glucans are used clinically to treat cancer in Japan, including PSK (from *Coriolus versicolor*), Lentinan and Schizophyllan. In randomized trials in Japan, PSK has moderately improved survival rates in some cancer trials after gastrectomy[3,4], colorectal surgery[5,6], and esophagectomy[7] to remove primary tumors. Results have been less encouraging in breast cancer[8,9] and leukemia[10]. Schizophyllan also moderately improved survival of patients with operable gastric cancer[11], inoperable gastric cancer[12,13], and cervical cancer[14]. While beta-glucans are not widely used by Western oncologists, beta-glucan containing botanical medicines such as Reishi and maitake[15] are widely used by U.S. cancer patients as alternative/complementary cancer therapies.

In Europe and USA, beta-glucans especially from Bakers' yeast have long been employed as feed additives for animals, as dietary supplement for humans[17], in treatment of wounds[18], and as an active ingredient in skin cream formulations. The basic structural unit in beta-glucans is the β(1→3)-linked glucosyl units. Depending upon the source and method of isolation, beta-glucans have various degrees of branching and of linkages in the side chains. The frequency and hinge-structure of side chains determine its immunomodulatory effect. Beta-glucans of fungal and yeast origin are normally insoluble in water, but can be made soluble either by acid hydrolysis or by derivatization introducing charged groups like -phosphate, -sulphate, -amine, -carboxymethyl and so forth to the molecule[19-20].

Previous studies that looked for a therapeutic effect of beta-glucan did not incorporate co-administration of therapeutic monoclonal antibodies (MoAb) as part of the protocol. When beta-glucan is administered without co-administration of MoAb, its tumor cytotoxic effect requires the presence of naturally-occurring antitumor antibodies which can be quite variable among patients and even in experimental mice. Thus, it is of interest to determine the therapeutic effects of co-administering beta-glucan and therapeutic monoclonal antibodies. It is also not clear whether therapeutic effect can be obtained by orally administered beta-glucan.

SUMMARY OF THE INVENTION

This invention provides a composition comprising an effective amount of yeast beta-glucan capable of enhancing immune responses in a subject or a host. In one embodiment, the enhanced immune responses are antitumor immune responses, which can be induced or initiated by various techniques or procedures generally known in the art. For example, antitumor immune responses can be induced by antitumor antibodies, cancer vaccines, or other compositions intended to induce immune responses against cancer.

In one embodiment, the present invention provides a yeast beta-glucan composition capable of enhancing the efficacy of antitumor antibodies and/or their derivatives. In another embodiment, the present invention provides a yeast beta-glucan composition capable of enhancing the efficacy of cancer vaccines, or the efficacy of other compositions intended to induce immune responses against cancer.

Antibodies as used herein refer to any part of immunoglobulin molecules (e.g. a monoclonal antibody) having specific cancer cell binding affinity by which they are able to exercise anti-tumor activity. Examples are antigen binding fragments or derivatives of antibodies. Furthermore, the antibody used in the present invention can be a single monoclonal antibody or a combination of antibodies. The antibodies may be directed to at least one epitope or multiple epitopes of an antigen or multiple antigens. Accordingly, this invention encompasses at least one antibody.

The cancer recognized by antibodies includes, but not limited to, neuroblastoma, melanoma, non-Hodgkin's lymphoma, Epstein-Barr related lymphoma, Hodgkin's lymphoma, retinoblastoma, small cell lung cancer, brain tumors, leukemia, epidermoid carcinoma, prostate cancer, renal cell carcinoma, transitional cell carcinoma, breast cancer, ovarian cancer, lung cancer colon cancer, liver cancer, stomach cancer, and other gastrointestinal cancers.

It will be recognized by one of skill in the art that the various embodiments of the invention relating to specific methods of treating tumors and cancer disease states may relate within context to the treatment of a wide number of other tumors and/or cancers not specifically mentioned herein. Thus, it should not be construed that embodiments described herein for the specific cancers mentioned do not apply to other cancers.

This invention further provides the above compositions and a pharmaceutically acceptable carrier, thereby forming pharmaceutical compositions.

This invention also provides a method for treating a subject with cancer, comprising administrating the above-described composition to the subject.

In one embodiment, the present invention provides a method for enhancing tumoricidal activities of antitumor antibody in a subject having cancer. In general, examples of cancer include, but are not limited to, neuroblastoma, melanoma, non-Hodgkin's lymphoma, Epstein-Barr related lymphoma, Hodgkin's lymphoma, retinoblastoma, small cell lung cancer, brain tumors, leukemia, epidermoid carcinoma, prostate cancer, renal cell carcinoma, transitional cell carcinoma, breast cancer, ovarian cancer, lung cancer, colon cancer, liver cancer, stomach cancer, or other gastrointestinal cancers.

The above method comprises the steps of (a) administering to the subject antitumor antibody that binds to cancer cells in the subject; and (b) administering orally to the subject a composition comprising an effective amount of yeast glucan, wherein the orally administered glucan enhances tumoricidal activities of the antibody. In general, the antibody is a monoclonal antibody. More preferably, the antibody is capable of activating complement or activating antibody dependent cell-mediated cytotoxicity. Representative examples of antitumor antibodies include, but are not limited to, antibodies that recognize CD20, CD22, HER-2/neu, CD25, epidermal growth factor receptor, or gangliosides.

In another embodiment, the yeast glucan used in the above method has an average molecular weight of about 16,000 to about 17,000 daltons, with a range from about 6,000 to about 30,000 daltons, or from about 6,000 to about 25,000 daltons. The yeast glucan can be administered at the same or different time as the administration of the antitumor antibody. Preferably, the yeast glucan is capable of priming or inducing secretion of cytokines, chemokines or growth factors by leukocytes.

The present invention also provides a therapeutic regimen for a subject having cancer, the regimen comprising a cooperative anti-cancer effect resulting from administering to a subject in need thereof: (i) antitumor antibody that binds to cancer cells in the subject, or a cancer vaccine composition intended to induce antitumor immune responses; and (ii) an effective amount of yeast glucan which is administered to the subject orally, wherein the orally administered glucan enhances tumoricidal activities of the antibody or the cancer vaccine composition. The yeast glucan can be administered at the same or different time as the administration of the antitumor antibody or the cancer vaccine. Examples of antitumor antibodies and yeast glucan have been described above. In general, examples of cancer vaccine include whole tumor cells, tumor cell lysates, tumor cell derived RNAs, tumor cell derived proteins, tumor cell derived peptides, tumor cell derived carbohydrates, tumor cell derived lipids, tumor cell derived DNA sequences and gene modified tumor cells, either clinically synthesized or recombinant products to serve as tumor anti-genes. These tumor cells could be derived from a patient's own tumor or tumor from an unrelated donor.

The present invention also provides uses of an effective amount of yeast glucan for preparing an anti-cancer pharmaceutical composition. The glucan is administered to a subject orally to enhance tumoricidal activities in the subject. The anti-cancer pharmaceutical composition may further comprise antitumor antibodies that bind to cancer cells in the subject, or a cancer vaccine composition intended to induce antitumor immune responses. The yeast glucan can be administered to a subject at the same or different time as the administration of the antitumor antibody or the cancer vaccine. Representative examples of antitumor antibodies, cancer vaccine, and yeast glucan have been described above.

DETAILED DESCRIPTION OF THE FIGURES

FIG. 1 shows treatment of disseminating human lymphoma in SCID mice using Rituxan and barley or yeast β-glucan. Five millions Daudi cells in 100 μl normal saline were injected intravenously (i.v.) into SCID mice. Tumors grew systemically and the mice became paralyzed when tumor cells infiltrated the spinal canal, resulting in hind-leg paralysis. The mice were sacrificed at the onset of paralysis or when the animals lost 10% of their body weight. Therapy was initiated ten days after injection of tumor cells. Forty μg rituximab (Genentech, San Francisco, Calif.) was injected intravenously twice weekly for a total of eight injections and 400 μg glucan was administered orally via intragastric gavage daily for 29 days. The mice were weighed weekly and observed clinically at least once daily. Mice receiving rituxan plus barley glucan or rituxan plus yeast soluble glucan have a highly significant prolonged survival (p<0.05).

FIG. 3 shows viscosity profile of SBG. Profiles for a 2% solution of SBG at 20 or 30° C. at different shear rates were shown. Glycerol (87%) was used as reference solution.

DETAILED DESCRIPTION OF THE INVENTION

The following terms shall be used to describe the present invention. In the absence of a specific definition set forth herein, the terms used to describe the present invention shall be given their common meaning as understood by those of ordinary skill in the art.

In the present invention the meaning of the expression "higher order conformation" defines the formation of a molecule by transformation of a collection of free atoms, which find themselves in a random spatial configuration, into a more stable non-random pattern of those same atoms. In other words, these atoms have connected themselves to each other, resulting in a new molecule, a new totality. The connection in this case is chemical, i.e. by means of chemical bonds like hydrogen bonds. Several of such molecules can in turn react with each other, resulting in other molecules, either of the same size, or possibly of a larger size. Both are new totalities again. The larger molecules are higher-order totalities.

In the present invention the expression "immunostimulating" refers to stimulating the immune system by inducing activation or increasing activity of any components of the immune system.

In the present invention the expression "immunopotentiating" refers to the activities of one substance that enhance or increase the immunostimulating effects of another substance.

The ability of beta-glucan to have immunopotentiating activity is likely the result of its ability to present multiple epitopes for interaction with receptors on the target cells, thereby clustering beta-glucan receptors and mimicking the challenge by a pathogenic organism. Such multiple interactions with specific receptors on the cell are believed to depend partly on glucan's ability to form "higher order" structures presenting multiple binding epitopes in close vicinity. Soluble beta-glucan formulations which possess durable interchain associations, as expressed by a high viscosity profile, would thus be likely candidates for expressing "immunpotentiating" abilities.

The term "cancer" refers to pathological process that results in the formation and growth of a cancerous or malignant neoplasm.

The term "effective amount" is used to describe that amount of a compound, when administered to an animal or a human, would lead to suppression or eradication of tumor growth or spread of the cancer, or other desirable immune responses.

The term "animal" is used to describe an animal, preferably a mammal, more preferably a human, to whom treatment or method according to the present invention is provided.

As used herein, the term "pharmaceutically acceptable carrier, additive or excipient" means a chemical composition with which an appropriate glucan or derivative may be combined and which, following the combination, can be used to administer the appropriate glucan to treat animals, preferable mammals, and most preferably humans.

Figure 1:
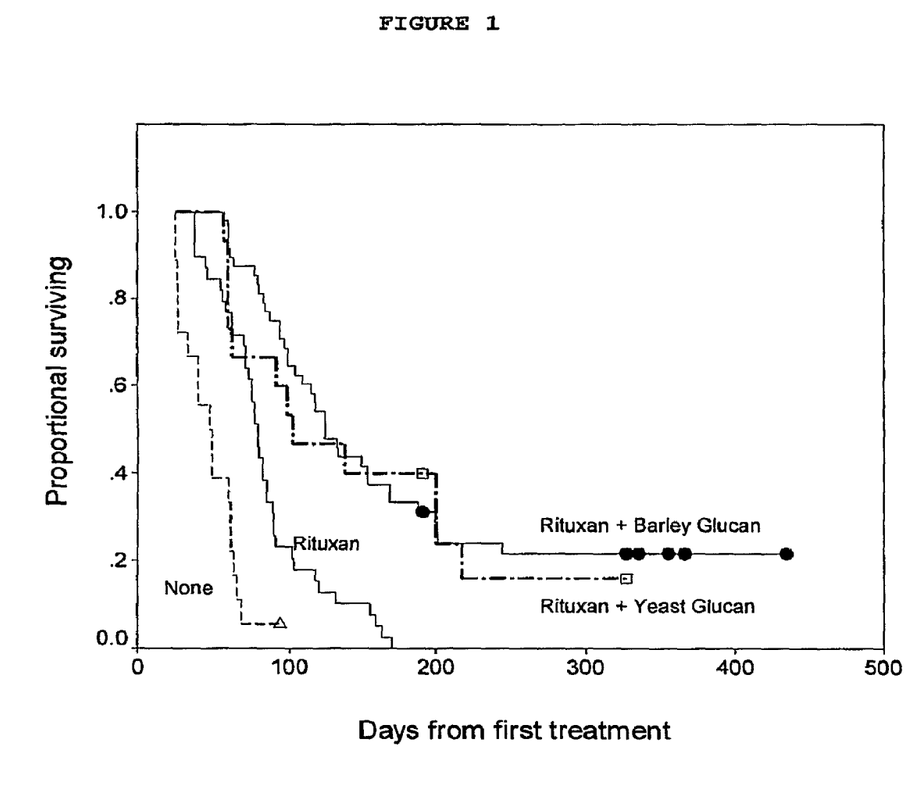

Previously it was shown in International Applications Nos. PCT/US02/01276 and PCT/US04/23099 that oral administrated beta-1,3 and 1,4-glucans with high molecular weight and high viscosity profile isolated from barley was effective in enhancing the efficacy of i.v. administered antibodies in eradication or suppression of cancer or tumor cells. It was also shown that a composition of yeast soluble beta-glucans with beta-1,3-linkages and specific types of side chains, thereby giving a higher order conformation with a higher viscosity profile than those used previously, surprisingly are equally active as barley-derived beta-glucans (see FIG. 1). The disclosures of PCT/US02/01276 and PCT/US04/23099 in their entireties are hereby incorporated by reference into this application.

It is generally accepted that beta-glucans of microbial origin, like yeasts, are recognised by specific pattern recognition receptors on immune cells as a result of phylogenetic adaptation for detecting possible pathogens. Beta-glucans in e.g. fungal cell walls are major structural element that secure the strength and integrity of the cell and are thus vital for the organism. Beta-1,3-glucans are present in almost all fungal cells and they are highly conserved structures, the latter being a prerequisite for the so-called Pathogen Associated Molecular Patterns (PAMPs) recognised by the immune system. Immunologically active beta-glucans are likely to bind to beta-glucan receptor known as Dectin-1 when introduced to the organism through the gastrointestinal tract.

Purified beta-1,3-glucans having the structural elements and conformations mimicking its fungal origin as being recognised by the immune cells would thus be considered favourable with respect to achieving an immune activation, especially when administered orally. It is likely that beta-1,3 and 1,4 glucans, although not derived from a microbial organism, would interact with the immune cells based on its similarity to conserved structures on pathogenic organisms. Examples of useful beta-glucans include, but are not limited to, particulate and soluble yeast cell wall glucans as described in PCT/IB95/00265 and EP 0759089. Other beta-1,3-glucan compositions having the ability to form interchain associations, as exemplified in having a high viscosity profile as described for the barley beta-1,3-1,4-glucan preparations, would also be suitable candidates. Specific preparations of e.g. lentinan, scleroglucan and schizophyllan showing durable interchain interactions are likely to be effective. Likewise, beta-1,3-glucan formulations solubilized by derivatization, like glucan phosphates, glucan sulphates, carboxymethyl-glucans, and retaining the immunopotentialing activity of the native molecule and interchain association would be possible active products.

Beta-glucan formulations not presenting a pathogen-like feature could nevertheless be potent adjuvants for immunotherapy when administered directly into systemic distribution, like when given i.v. as described in Herlyn et al. (Monoclonal antibody-dependent murine macrophage-mediated cytotoxicity against human tumors is stimulated by lentinan. *Jpn. J. Cancer Res.* 76, 37-42 (1985)), or when given i.p. as described in U.S. Ser. No. 60/261,911.

Figure 4:
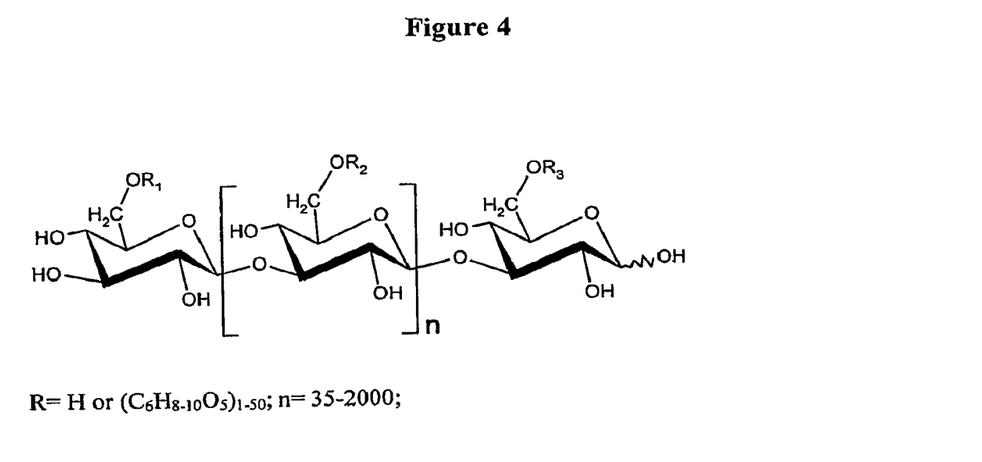
FIG. 4 shows beta-glucan comprising a beta-1,3-linked backbone.

In one embodiment, the present invention discloses a composition for achieving a synergistic therapeutic effect in an animal, preferably a mammal, most preferably a human in need thereof, comprising (i) a viscous and immunopotentiating yeast beta-glucan composition comprising a beta-1,3-linked backbone as shown in FIG. 4 and (ii) an antitumor antibody, wherein the synergistic therapeutic effect is the eradication or suppression of cancer or tumor cells. The ability of yeast beta-glucans to have immunopotentiating activity is likely due to their ability to present multiple epitopes for interaction with receptors on the target cells, thereby clustering beta-glucan receptors and mimicking the challenge by a pathogenic organism. Such multiple interactions with specific receptors on the cell are believed to depend partly on beta-glucan's ability to form "higher order" structures presenting multiple binding epitopes in close vicinity. Soluble beta-glucan formulations which possess durable interchain associations, as expressed by a high viscosity profile, would also likely be candidates for expressing "immunpotentiating" abilities.

In one embodiment, the beta-glucan composition comprises yeast beta-glucans with beta-1,3-linked main chain having a molecular weight (MW)>6000 Da, and has side chains attached thereto giving a soluble product with strong interchain associations. Representative examples include, but are not limited to, beta-1,3-glucans isolated from yeast with beta-1,3-linked side chains anchored to the main chain through beta-1,6-linkage (see FIG. 5). Suitable forms of yeast glucans include, but are not limited to, particulate, soluble, or gel form.

Figure 5:
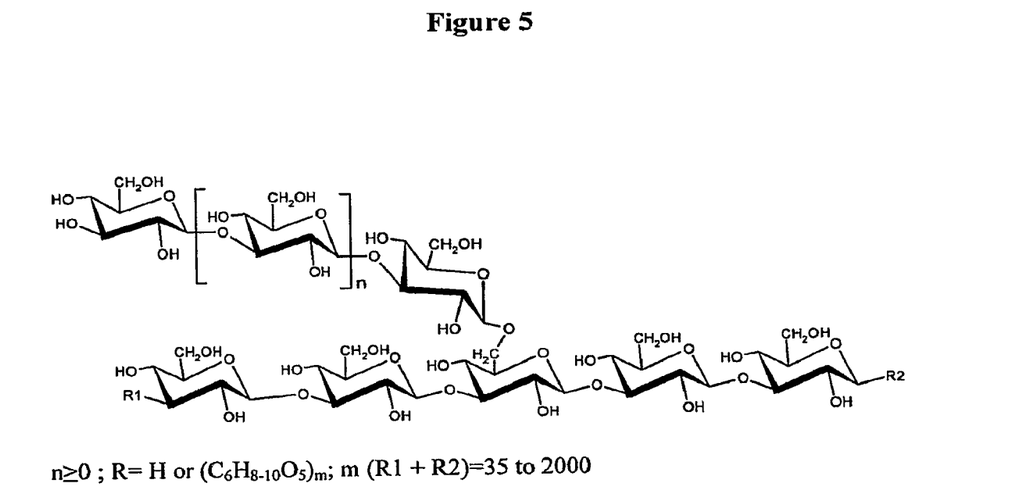
FIG. 5 shows beta-1,3-glucans isolated from yeast with beta-1,3-linked side chains anchored to the main chain through beta-1,6-linkage.

An example of a highly active composition of yeast beta-glucans is a mixture of soluble beta-glucan chains with molecular weight (MW)>6000 daltons that interact to give a higher order conformation which would exhibit immunostimulatory activity when administered orally to induce synergistic effect with the antibodies. In one embodiment, the mixture of soluble beta-glucans comprise linear beta-1,3-glucan chains with MW>6000 Da, or more preferably, with MW ranging from 6000-30,000 Da, together with branched high molecular weight beta-1,3-glucan (MW>15,000 Da) with beta-1,3 linked side chain(s) extending from within the main chain as shown in FIG. 5.

Figure 2:
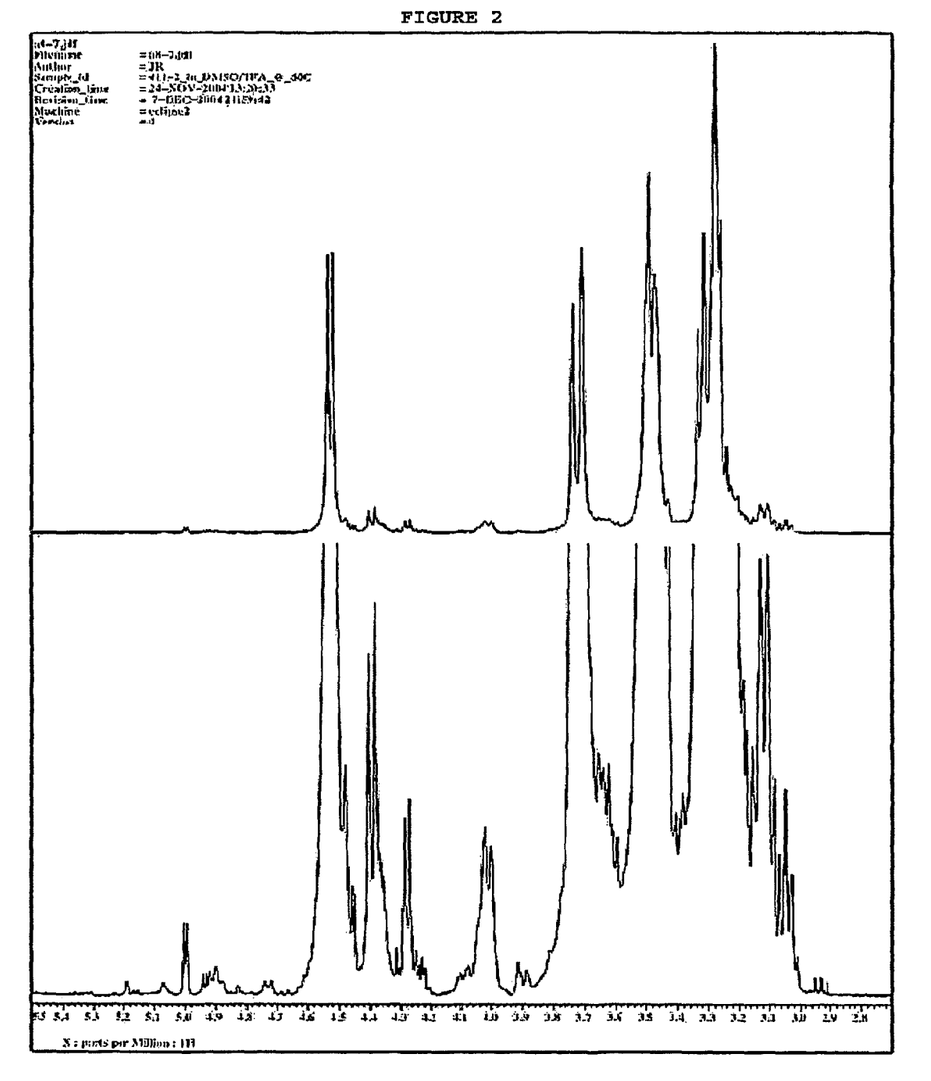
FIG. 2 shows $^1$H NMR spectrum of a typical SBG (Soluble Beta Glucan) sample (Biotec Pharamacon ASA, Tromsø, Norway). A SBG sample was dissolved in DMSO-$d_6$ at a concentration of approximately 20 mg/ml and with a few drops of TFA-d added. The spectrum (cut-out from 2.7 to 5.5 ppm) was collected over 2 hours on a JEOL ECX 400 NMR spectrometer at 80° C. Chemical shifts were referenced to residual proton resonance from the DMSO-$d_6$ at 2.5 ppm, and the spectrum was baseline corrected.
Figure 3:
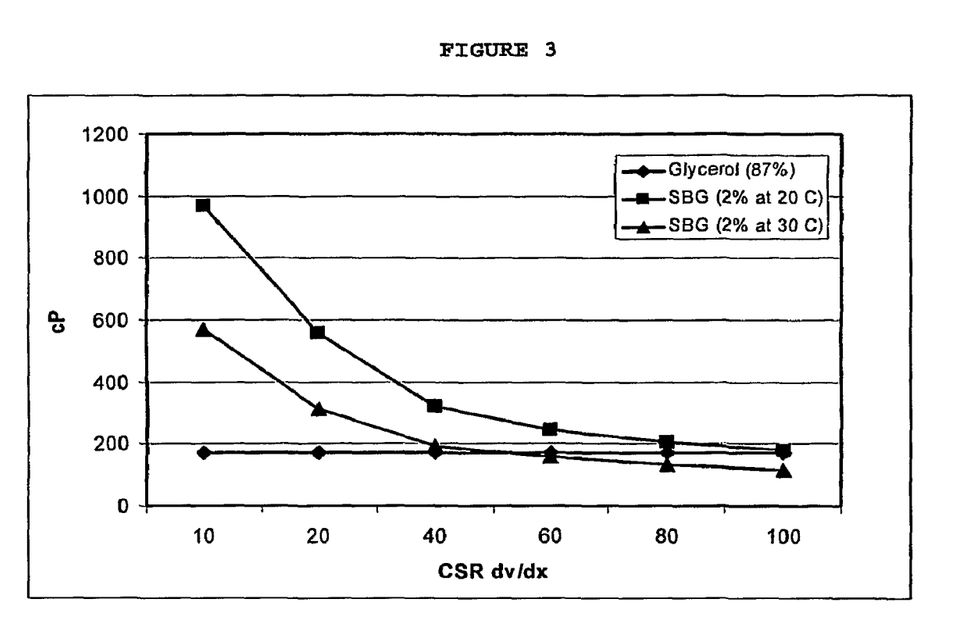

An example of the glucan as described above is SBG (Soluble Beta Glucan) produced by Biotec Pharamacon ASA (Tromsø, Norway). SBG, a pure natural product derived from Bakers' yeast, is an underivatized aqueous soluble β-1,3/1,6-glucan characterized by NMR and chemical analysis to consist of polymers of β-1,3-linked D-glucose containing side chains of β-1,3 and β-1,6-linked D-glucose (see FIG. 2). Preferably, the yeast glucans have an average molecular weight of about 16,000 to about 17,000 daltons, with a range from about 6,000 to about 30,000 daltons, or from about 6,000 to about 25,000 daltons As shown in FIG. 2, SBG shows a complex beta-glucan composition with high molecular weight chains having beta-1,3-linked side chains attached to the repeating beta-1,3-linked main chain through a beta-1,6-linked branching point, and medium molecular weight linear beta-1,3-glucan chains in the range of 6-15 kDa. SBG (Soluble Beta Glucan) presents durable interchain association as demonstrated by its high viscosity profile and gelling behavior (see FIG. 3). SBG has been shown to be a potent immunostimulating agent for activating human leukocytes in vitro, e.g. priming and inducing the production of cytokines (see Engstad et al. (2002) The effect of soluble beta-1,3-glucan and lipopolysaccharide on cytokine production and coagulation activation in whole blood. *Int. Immunopharmacol.* 2:1585-1597), and also for modulating immune functions when given p.o. (see Breivik et al. (2005) Soluble beta-1,3/1,6-glucan from yeast inhibits experimental periodontal disease in Wistar rats. *J. Clinical Periodontology* 32:347-3.). It is preferable for the yeast glucans of the present invention to have such functional properties of priming and inducing cytokine production by human leukocytes.

Other structures and/or structural conformations in the composition of beta-1,3-glucans as described above can be readily identified or isolated by a person of ordinary skill in the art following the teaching of this invention, and is expected to have similar therapeutic effect when administered through different routes other than p.o. The above is thus a guideline to achieve a highly potent product, but is not a limitation towards even more potent products. Isolated structural elements of the complex mixture as described above are expected to have improved effects over the present formulation when administered orally.

Products having the desired structural features giving a higher order conformation like SBG that facilitates the needed interaction with responding cells in the intestinal tract would be the preferred products when administered orally. Their action as immunopotentiators in synergy with anti-cancer antibodies is likely to be at least as powerful when administered parenterally, e.g. when administered i.p., s.c., i.m. or i.v. Functional dose range of the glucans can be readily determined by one of ordinary skill in the art. For example, when administered orally the functional dose range would be in the area of 1-500 mg/kg b.w. (body weight)/day, more preferable 10-200 mg/kg b.w./day, or most preferable 20-80 mg/kg/day. In another embodiment, when administered parenterally the functional dose range would be 0.1-10 mg/kg b.w./day.

Typically, dosages of the compound of the present invention administered to an animal, preferably a human, will vary depending upon any number of factors, including but not limited to, the type of animal and type of cancer and disease state being treated, the age of the animal, the route of administration and the relative therapeutic index.

The route(s) of administration will be readily apparent to the skilled artisan and will depend upon any number of factors including the type and severity of the disease being treated, the type and age of the human patient being treated, and the like.

Formulations suitable for oral administration of the beta-glucan include, but are not limited to, an aqueous or oily suspension, an aqueous or oily solution, or an emulsion. Such formulations can be administered by any means including, but not limited to, soft gelatin capsules.

Liquid formulations of a pharmaceutical composition of the present invention which are suitable for oral administration may be prepared, packaged, and sold either in liquid form or in the form of a dry product intended for reconstitution with water or other suitable vehicle prior to use.

In general, the beta-glucan can be administered to an animal as frequently as several times daily, or it may be administered less frequently, such as once a day. The antibody treatment will for instance depend upon the type of antibody, the type of cancer, the severity of the cancer, and the condition of each patient. The beta-glucan treatment is closely interrelated with the antibody treatment regimen, and could be ahead of, concurrent with, or after the antibody administration. The frequency of the beta-glucan and antibody dose will be readily apparent to the skilled artisan and will depend upon any number of factors, such as, but not limited to, the type and severity of the disease being treated, and the type and age of the patients. Treatment with the substance of the present invention could happen at the same time or at different times. For example, the beta-glucan treatment could start a few days ahead of the i.v. antibody treatment, and then the beta-glucan is administered concurrently with the antibody. In another embodiment, beta-glucan treatment may continue for a few days after ending the antibody treatment. The antibody treatment could include a cocktail of antibodies or antibody-formulations, modified antibodies and/or derivatives thereof.

When administered orally, glucan is taken up by macrophages and monocytes that carry these carbohydrates to the marrow and reticuloendothelial system from where they are released, in an appropriately processed form, onto myeloid cells including neutrophils and onto lymphoid cells including natural killer (NK) cells. The processed glucan binds to CR3 on these neutrophils and NK cells, and activating their anti-tumor cytotoxicity in the presence of tumor-specific antibodies.

The present invention provides a composition comprising an effective amount of orally administered (1→3),(1→6) beta-glucan capable of enhancing the efficacy of antitumor antibodies. Glucans derived from cell walls of yeasts, such as *Saccharomyces cervisiae*, may be used in the above-described compositions. Preferably, glucans having β(1-3) and β(1-6) linkages, such as SBG (Soluble Beta Glucan) produced by Biotec Pharamacon ASA (Tromsø, Norway), is used in the above-described compositions. The above mentioned pharmaceutical compositions may contain pharmaceutically acceptable carriers and other ingredients known to enhance and facilitate drug administration. The relative amounts of the active ingredient, the pharmaceutically acceptable carrier, and any additional ingredients in a pharmaceutical composition of the invention will vary, depending upon the identity, size, and condition of the subject treated.

Such a pharmaceutical composition may comprise the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in forms which are generally well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit. Controlled- or sustained-release formulations of a pharmaceutical composition of the present invention may be made using conventional technology.

In one embodiment, the above glucan composition may comprise a monoclonal antibody, or an antibody against cancer or tumor cells, which include but are not limited to anti-CEA antibody, anti-CD20 antibodies, anti-CD25 antibodies, anti-CD22 antibodies, anti-HER2 antibodies, anti-tenascin antibodies, MoAb M195, Dacluzimab, anti-TAG-72 antibodies, R24, Herceptin, Rituximab, 528, IgG, IgM, IgA, C225, Epratuzumab, MoAb 3F8, and antibody directed at the epidermal growth factor receptor, or a ganglioside, such as GD3 or GD2. In another embodiment, the antibody is a tumor-binding antibody. Preferably, the antibody is capable of activating complement and/or activating antibody dependent cell-mediated cytotoxicity. In a further embodiment, the antibody modulates T-cell or B-cell function.

In general, the antibodies are effective against cancers which include neuroblastoma, melanoma, non-Hodgkin's lymphoma, Epstein-Barr related lymphoma, Hodgkin's lymphoma, retinoblastoma, small cell lung cancer, brain tumors, leukemia, epidermoid carcinoma, prostate cancer, renal cell carcinoma, transitional cell carcinoma, breast cancer, ovarian cancer, lung cancer, colon cancer, liver cancer, stomach cancer, or other gastrointestinal cancers.

The present invention also provides a method for treating a subject comprising administrating the above-described composition to a subject.

The present invention also provides a composition comprising an effective amount of orally administered (1→3), (1→6) beta-glucan capable of enhancing the efficacy of vaccines. In one embodiment, the vaccine is against cancer or infectious agents, such as bacteria, viruses, fungi, or parasites.

The present invention also provides a composition comprising an effective amount of orally administered (1→3), (1→6) beta-glucan capable of enhancing host immunity. The host immunity includes, but is not limited to, antitumor immune responses.

In another embodiment, the present invention provides a composition comprising an effective amount of orally administered (1→3),(1→6) beta-glucan capable of enhancing the action of an agent in preventing tissue rejection. In one embodiment, the tissue is transplanted tissue or transplanted organ or the host of graft-versus-host disease.

This invention also provides kits for inhibiting cancer cell growth and/or metastasis. The invention includes a kit or an administration device comprising a glucan as described herein and information material which describes administering the glucan or a composition comprising the glucan to a human. The kit or administration device may have a compartment containing the glucan or the composition of the present invention. As used herein, the "Information material" includes, but is not limited to, a publication, a recording, a diagram, or any other medium of expression which can be used to communicate the usefulness of the composition of the invention for its designated use.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Example 1

Yeast β-Glucan Enhances Immune Responses

Whole tumor vaccines can induce tumor-specific protective immunity in preclinical tumor models. Recent clinical trials using GM-CSF-modified allogeneic or syngeneic tumor lines have yielded positive although modest clinical responses. When one reviews successful vaccines in human medicine, evidence continues to point to the importance of antibodies in both the induction as well as the maintenance of protective immunity. The persistence of cancer remission long after the completion of monoclonal antibodies strongly suggests an active immunity induced by "passive antibody therapy". It is postulated that tumor vaccines when opsonized with specific antibodies will enhance their presentation to antigen presenting cells. In the presence of β-glucan, the efficacy of such vaccines can be further improved.

The EL4 syngeneic mouse model of lymphoma was used to study antibody response to whole tumor vaccine in the presence of β-glucan. When live EL4 tumor cells were planted subcutaneously or intravenously in immunocompetent C57Bl/6 mice, they engrafted rapidly causing death from large tumor masses and metastases to distant organs. When EL4 tumor cells were planted subcutaneously or intravenously in the presence of anti-GD2 antibody 3F8, tumor cell engraftment diminished. When challenged later with EL4 cells, there was marginal protective immunity. Since β-glucan is known to activate antigen-presenting cells, EL4 cells were administered in the presence of 3F8 as a tumor vaccine to test if β-glucan can provide adjuvant effect to induce protective immunity.

C57Bl/6 mice were vaccinated subcutaneously with EL4 lymphoma (as whole tumor vaccine) in the presence of anti-GD2 antibody 3F8 plus yeast β-glucan. Mouse sera were obtained at week 2, 4, and 8 after vaccination. Serum antibodies against surface antigens on EL4 cells were assayed by flow cytometry. Antibodies against total cell antigens (surface and cytoplasmic) were assayed by ELISA using EL4 cells bound to microtiter plates.

Results from these experiments indicate that: (1) 3F8 was necessary to prevent subcutaneous EL4 tumor engraftment; (2) 3F8 enhanced antibody response to EL4 whole tumor vaccine; (3) live EL4 tumor vaccine stimulated a significantly higher immune response compared to irradiated EL4 tumor vaccine; (4) antibody titer against EL4 tumor increased with increasing dose of glucan as an adjuvant, with an optimal dose at 2 mg; and (5) the higher the dose of glucan, the longer the mice were protected when subsequently challenged with intravenous EL4 in a tumor prevention model.

Example 2

Phase I Study of Orally Administered Yeast β-Glucan

In this phase I study, patients with refractory or recurrent metastatic stage 4 neuroblastoma were recruited. They all received anti-GD2 antibody 3F8 at 10 mg/m2/day for a total of 10 days, while being given oral yeast β-glucan. The dose of yeast β-glucan was escalated in cohorts of 3-6 patients (10, 20, 40, 80, 100, 120 mg/kg/dose). Eighteen patients have been registered. There were no dose limiting toxicities (DLTs).

Three (3) patients were registered and treated at 10 mg/kg dose level. These patients have completed all four cycles of treatment. Two of these three patients showed a minor response. One patient had progressive disease.

Three (3) patients were registered and treated at the 20 mg/kg dose level. One (1) completed all four cycles with an objective response and had an additional four cycles of treatment approved by IRB. He is now completing cycle 6. One (1) patient has completed all four cycles and undergoing extent of disease evaluation. One (1) patient completed three (3) cycles of treatment and then developed human anti-mouse response (HAMA). Extent of disease evaluation is pending.

Three (3) patients were registered and treated at the 40 mg/kg dose level. One (1) completed all four cycles of treatment. Extent of disease evaluation at the end of four cycles revealed progression of disease. One (1) patient completed one cycle of treatment. Extent of disease evaluation after one cycle revealed progressive disease. One (1) patient is now completing cycle 3.

Six (6) patients have been registered and treated at the 80 mg/kg dose level. One (1) of the patients completed all four cycles of treatment and extent of disease evaluation and had a very good partial response (VGPR). One (1) patient completed two cycles. Extent of disease evaluation after two cycles revealed progressive disease. Two (2) patients completed only one cycle of treatment and had progressive disease after one cycle. One (1) patient is receiving cycle 2 of treatment. One (1) patient has completed one cycle of treatment. The latter two patients continue on protocol.

Three (3) patients were registered and treated at the 100 mg/kg dose level. There were no dose limiting toxicities. One patient (1) has progressed. One (1) patient achieved a complete remission of marrow disease. The last patient was still too early to be evaluated for response. The latter two patients continue on protocol.

REFERENCES

1. Diller, I. C., Mankowski, Z. T., and Fisher, M. E. The effect of yeast polysaccharides on mouse tumors. Cancer Res, 23: 201-208, 1963.
2. Sveinbjornsson, B., Rushfeldt, C., Seljelid, R., and Smedsrod, B. Inhibition of establishment and growth of mouse liver metastases after treatment with interferon gamma and beta-1,3-D-Glucan. Hepatology, 27(5): 1241-1248, 1998.
3. Niimoto, M., Hattori, T., Tamada, R., Sugimachi, K., Inokuchi, K., and Ogawa, N. Postoperative adjuvant immunochemotherapy with mitomycin C, futraful, and PSK for gastric cancer. An analysis of data on 579 patients followed for five years. Japanese Journal of Surgery, 18: 681-686, 1988.
4. Nakazato, H., Koike, A., Saji, S., Ogawa, N., and Sakamoto, J. Efficacy of immunochemotherapy as adjuvant treatment after curative resection of gastric cancer. Study Group of Immunochemotherapy with PSK for Gastric Cancer. Lancet, 343: 1122-1126, 1994.
5. Torisu, M., Hayashi, Y., Ishimitsu, T., Fujimura, T., Iwasaki, K., Katano, M., Yamato, H., Kimura, Y., Takesue, M., and Kondo, M. Significant prolongation of disease-free period gained by oral polysaccharide K (PSK) administration after curative surgical operation of colorectal cancer. Cancer Immunol. Immunother., 31: 261-268, 1990.
6. Mitomi, T., Tsuchiya, S., Tijima, N., Aso, K., Suzuki, K., Nishiyama, K., Amano, t., Takahashi, T., Murayama, N., and Oka, H. Randomized, controlled study on adjuvant immunochemotherapy with PSK in curatively resected colorectal cancer. The cooperative study group of surgical adjuvant immunochemotherapy for cancer of colon and rectum (Kanagawa). Dis Colon Rectum, 35; 123-130, 1992.
7. Ogoshi, K., Satou, H., Isono, K., Mitomi, T., Endoh, M., and Sugita, M. Immunotherapy for esophageal cancer. A randomized trial in combination with radiotherapy and radiochemotherapy. Cooperative study group for esophageal cancer in Japan. American Journal of Clinical Oncology, 18: 216-222, 1995.
8. Toi, M., Hattori, T., Akagi, M., Inokuchi, K., Orita, K., Sugimachi, K., Dohi, K., Nomura, Y., Monden, Y., and Hamada, Y. Randomized adjuvant trial to evaluate the addition of tamoxifen and PSK to chemotherapy in patients with primary breast cancer. 5-year results from the Nishi-Nippon group of the adjuvant chemoendocrine therapy for breast cancer organization. Cancer, 70: 2475-2483, 1992.
9. Lino, Y., Yokoe, T., Maemura, M., Horiguchi, J., Takei, H., Ohwada, S., and Morishita, Y. Immunochemotherapies versus chemotherapy as adjuvant treatment after curative resection of operable breast cancer. Anticancer Res., 15: 2907-2911, 1995.
10. Ohno, R., Yamada, K., Masaoka, T., Ohshima, T., Amaki, I., Hirota, Y., Horikoshi, N., Horiuchi, A., Imai, K., and Kimura, I. A randomized trial of chemoimmunotherapy of acute nonlymphocytic leukemia in adults using a protein-bound polysaccharide preparation. Cancer Immunol Immunother, 18: 149-154, 1984.
11. Fujimoto, S., Furue, H., Kimura, T., Kondo, T., Orita, K., Taguchi, T., Yoshida, K., and Ogawa, N. Clinical outcome of postoperative adjuvant immunochemotherapy with sizofuran for patients with resectable gastric cancer: a randomised controlled study. Eur J Cancer, 27: 1114-1118, 1991.
12. Furue, H., Uchino, H., Orita, K., Kimura, T., Goto, Y., Kondo, T., Sato, S., Takino, T., Taguchi, T., Nakao, I., and al., e. Clinical evaluation of schizophyllan (SPG) in advanced gastric cancer (the second report)—a randomized controlled study. Gan To Kagaku Ryoho, 12: 1272-1277, 1985.
13. Nakao, I., Uchino, H., Orita, K., Kaido, I., Kimura, T., Goto, Y., Kondo, T., Takino, T., Taguchi, T., Nakajima, T., Fujimoto, S., Miyazaki, T., Miyoshi, A., Yachi, A., Yoshida, K., Ogawa, N., and Furue, H. Clinical evaluation of schizophyllan (SPG) in advanced gastric cancer—a randomized comparative study by an envelop method. Jpn J Cancer Chemother, 10: 1146-1159, 1983.
14. Okamura, K., Suzuki, M., Chihara, T., Fujiwara, A., Fukada, T., Goto, S., Ichinohe, K., Jimi, S., Kasamatsu, T., and Kawai, N. Clinical evaluation of sizofuran combined with irradiation in patients with cervical cancer. A randomized controlled study; a five-year survival rate. Biotherapy, 1: 103-107, 1989.
15. Mayell, M. Maitake extracts and their therapeutic potential. Altern Med Rev, 6: 48-60, 2001.
16. Engstad, R. and J. Raa., "Immune-stimulation improving health and performance. Feed Magazine (Kraftfutter) 7-8, 261-266 1999, Ref Type: Magazine Article
17. Nicolosi, R., S. J. Bell, B. R. Bistrian, I. Greenberg, R. A. Forse, and G. L. Blackburn 1999. "Plasma Lipid changes after supplementation with beta-glucan fiber from yeast. Am. J. Clin. Nutr 70 208-212
18. Kernodle, D. D., H. Gates, and A. B. Kaiser. 1998. Prophylactic Anti-Infective Activity of Poly-[1-6]-D-Glucopyranosyl-[1-3]-D-Glucopyranose Glucan in a Guinea Pig Model of Staphylococcal Wound Infection. Antimicrobial Agents and Chemotherapy 42: 545-549
19. Seljelid, R. 1986. "A water soluble aminated β-1,3-D-glucose derivative caused regression of solid tumors in mice. Bioscience Reports 6:845-852
20. Williams, D. L., H. A. Pretus, R. B. McNamee, E. L. Jones, H. E. Ensley, I. W. Browder, and N. R. Di Luzio 1991. "Development, physicochemical characterization and preclinical efficacy evaluation of a water soluble glucan sulfate derived from Saccharomyces cerevisiae. Immunopharmacology 22: 139-155

What is claimed is:

1. A method of treating cancer in a subject, comprising administering to the subject:
   (a) an antitumor antibody that binds to cancer cells expressing an antigen selected from the group consisting of CD20, CD22, CD25, HER2, EGFR, GD2, and GD3; and
   (b) a composition comprising an effective amount of a β-glucan, wherein the β-glucan enhances the anti-tumor activity of said antibody, wherein the β-glucan comprises a β-1,3 backbone and at least one β-1,3 side chain of two or more glucose units linked to the backbone by β-1,6 glycosidic bonds, and wherein the β-glucan has a molecular weight from about 6 kDa to about 30 kDa.
2. The method of claim 1, wherein the β-glucan is isolated from yeast.
3. The method of claim 1, wherein the β-glucan is isolated from *Saccharomyces Cerevisiae*.
4. The method of claim 1, wherein the β-glucan is a particulate or soluble glucan, capable of inducing cytokines.
5. The method of claim 1, wherein the antibody is a monoclonal antibody or complement-activating antibody.

6. The method of claim 1, wherein the antibody is capable of activating an antibody dependent cell-mediated cytotoxicity.

7. The method of claim 1, wherein the β-glucan is administered orally or intravenously.

8. A method of treating cancer in a subject, comprising administering to the subject:
(a) an antitumor antibody that binds to cancer cells of neuroblastoma, melanoma, non-Hodgkin's lymphoma, breast cancer, Epstein-Barr related lymphoma, Hodgkin's lymphoma, and epidermoid carcinoma; and
(b) a composition comprising an effective amount of a β-glucan, wherein the β-glucan enhances the anti-tumor activity of said antibody, wherein the β-glucan comprises a β-1,3 backbone and at least one β-1,3 side chain of two or more glucose units linked to the backbone by β-1,6 glycosidic bonds, and wherein the β-glucan has a molecular weight from about 6 kDa to about 30 kDa.

9. The method of claim 8 wherein the β-glucan is isolated from yeast.

10. The method of claim 8, wherein the β-glucan is isolated from *Saccharomyces Cerevisiae*.

11. The method of claim 8, wherein the β-glucan is a particulate or soluble glucan, capable of inducing cytokines.

12. The method of claim 8, wherein the antibody is a monoclonal antibody or complement-activating antibody.

13. The method of claim 8, wherein the antibody is capable of activating an antibody dependent cell-mediated cytotoxicity.

14. The method of claim 8, wherein the β-glucan is administered orally or intravenously.

* * * * *

UNITED STATES PATENT AND TRADEMARK OFFICE
CERTIFICATE OF CORRECTION

| | |
|---|---|
| PATENT NO. | : 8,323,644 B2 |
| APPLICATION NO. | : 12/161285 |
| DATED | : December 4, 2012 |
| INVENTOR(S) | : Nai-Kong V. Cheung et al. |

It is certified that error appears in the above-identified patent and that said Letters Patent is hereby corrected as shown below:

On Title Page 1, the following should be added.

-- Related U.S. Application Data (63) Continuation-in-part of application No. 11/334,763, filed on Jan. 17, 2006, now Pat. No. 7,906,492. --

On Title Page 6, left column, the fifth reference from the bottom,

"Chinese Office Action. Jul. 24," should be -- Chinese Office Action, Jul. 24, 2009, --

On Title Page 6, right column, the tenth reference from the top,

"Chinese Rejection Decision, Jan. 29:" should be -- Chinese Rejection Decision, Jan. 29, 2010, --

Signed and Sealed this
Fourth Day of June, 2013

Teresa Stanek Rea
*Acting Director of the United States Patent and Trademark Office*